United States Patent [19]

Daniels

[11] 4,292,040
[45] Sep. 29, 1981

[54] ISOLATION AND DETERMINATION OF NITROSOAMINES

[75] Inventor: Robert J. Daniels, Florissant, Mo.

[73] Assignee: Monsanto Company, St. Louis, Mo.

[21] Appl. No.: 163,746

[22] Filed: Jun. 27, 1980

[51] Int. Cl.$^3$ ...................... G01N 31/22; G01N 31/08
[52] U.S. Cl. .................................... 23/230 R; 252/408
[58] Field of Search ........................ 23/230 R, 230 PC

[56] References Cited

U.S. PATENT DOCUMENTS

| 3,973,910 | 8/1976 | Fine | 23/230 PC |
| 3,996,002 | 12/1976 | Fine | 23/230 PC |
| 3,996,004 | 12/1976 | Fine | 23/230 PC |
| 4,066,411 | 1/1978 | Fine | 23/230 PC |

OTHER PUBLICATIONS

G. M. Singer et al., J. Chromatogr., 133, 59–66 (1977).
M. J. Downes et al., Analyst, 101, 742–748 (1976).
C. L. Walters et al., Br. Food Manuf. Ind. Res. Assoc., Leatherhead, Surrey, Engl., IARC Sci. Publ., 75, 9 (N-Nitroso Compd. Environ., Proc. Work Conf., 1973) 22–25.
W. I. Stephen, Analyst, 102, 793–803 (1977).
B. E. Saltzman, Anal. Chem., 26 (12), 1949–1955 (1954).

Primary Examiner—Sidney Marantz
Attorney, Agent, or Firm—Gordon F. Sieckmann; Donald W. Peterson

[57] ABSTRACT

A method of determining the content of polar-substituted alkyl nitrosoamines in a sample at levels as low as 20 nanograms in the presence of interfering substances such as nitrites and the like. After chromatographic separation, the nitrosoamine is reacted with reagent comprising hydrogen bromide, sulfanilamide, hydrochloric acid, surfactant and N-(1-naphthyl)ethylenediamine to give a colored product.

4 Claims, No Drawings

ISOLATION AND DETERMINATION OF NITROSOAMINES

The invention relates to a method for quantitatively determining the nitrosoamine content of a sample. More particularly, the present invention is concerned with a method of determining the content of polar-substituted alkyl nitrosoamines at levels as low as 20 nanograms in the presence of interfering substances such as nitrites and the like.

In accordance with the method of the present invention, a sample containing the nitrosoamine of interest is chromatographically separated from interfering substances. The nitrosoamine is subjected to an acid catalyzed hydrolysis employing a hydrogen bromide-hydrogen chloride mixture at a temperature of 85°–95° C. The acid catalyzed hydrolysis results in the cleavage of the nitrogen-nitrogen bond of the nitrosoamine and the formation of nitrous acid ($HNO_2$). The nitrous acid thus formed promotes a diazo coupling reaction between sulfanilamide and N-(1-naphthyl)-ethylenediamine hydrochloride to produce a colored complex which can be spectrophotometrically measured. The amount of color complex formed correlates directly to the level of nitrosoamine in the original sample.

It is preferred that the chromatographic technique utilized to separate the nitrosoamines be high pressure liquid chromatography. It is more preferred that ion exchange high pressure liquid chromatography be employed. The chromatographic parameters such as column packing, column size, column temperature, carrier flow rate, pressure and the like, are dependent on factors such as the specific nitrosoamine to be determined, the level of nitrosoamine to be measured, the sensitivity desired, and the like. Selection of the proper chromatographic parameters are readily determined by one of ordinary skill in the art.

In order to maximize the formation of nitrous acid, the amount of hydrogen bromide-hydrogen chloride employed as the acid catalyst in the hydrolysis of the nitrosoamine should at least be equal to the content of the nitrosoamine in the sample. For maximum efficiency and accuracy, it is preferred to employ an amount of hydrogen bromide-hydrogen chloride which is in excess of the nitrosoamine content of the sample. To optimize formation of the diazo intermediate, it is necessary to employ an amount of sulfanilamide equal to the amount of nitrous acid produced. For maximum conversion of the nitrous acid to diazo intermediate, an excess of sulfanilamide should be employed. To optimize formation of the colored complex, an amount of N-(1-naphthyl)ethylene-diamine hydrochloride equal to the amount of diazo intermediate produced should be employed. To affect maximum conversion of the diazo intermediate to the respective colored complex, it is preferred to employ excess of N-(1-naphthyl)ethylenediamine hydrochloride. The colorimetric procedure in the method of the present invention can be employed utilizing a Technicon "Autoanalyzer ®" as illustrated in Example 1. The preparations of the reagents in the following example are readily ascertainable to one skilled in the art.

All reagents are introduced into the analyzer flow system by means of a peristalic pump. The flow rates, concentrations of the reagents and other variable parameters are only shown to exemplify the method of the present invention and are not to be considered limitations thereof.

EXAMPLE 1

| Reagents |
|---|
| Hydrobromic Acid, AR, 48% |
| N-(1-Naphthyl)Ethylenediamine, Dihydrochloride |
| Sulfanilamide, Hydrochloride Acid, AR |
| Brij 35 surfactant comprising a polyoxyethylene (23) lauryl ether 30% Solution Aqueous |
| Potassium Phosphate Monobasic, AR |
| Methanol, HPLC Grade |
| Phosphoric Acid, 85%, AR |
| Buffer Solution, pH 2.00 |
| Buffer Solution, pH 6.00 |

N-(1-Naphthyl)Ethylenediamine Dihydrochloride/Hydrogen Bromide Reagent Mixture To 450 ml. of water in a 1 liter volumetric flask add 4.35 g. of N-(1-naphthyl)ethylenediamine dihydrochloride (0.017 mol). The mixture is stirred until the N-(1-naphthyl)ethylenediamine dihydrochloride has dissolved. To the mixture is added 500 ml. of hydrogen bromide (3.0 mol) and the volume of the resulting mixture is taken up to 1 liter with distilled water. The resulting N-(1-naphthyl)ethylenediamine dihydrochloride/hydrogen bromide reagent mixture is stirred for an additional 15 minutes.

Sulfanilamide/Hydrochloric Acid/Brij 35 Reagent Mixture

To a 2 liter volumetric flask containing approximately 1500 ml. of distilled water is added 20.0 g. of sulfanilamide (0.116 mol), 66 ml. of Brij 35 and 200 ml. of concentrated hydrochloric acid. The resulting mixture is taken up to 2 liters with distilled water and then stirred until the sulfanilamide is completely dissolved.

The following chromatographic parameters can be utilized to separate and isolate polar-substituted alkyl nitrosoamines. Such polar-substituted alkyl nitrosoamines are characterized as having an acid hydrogen. Illustrative of the polar-substituted alkyl nitrosoamines is a compound of the formula

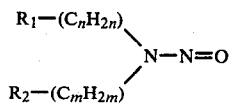

wherein n and m are independently integers from 1 to 6 and $R_1$ is a carboxy (—COOH), phosphonic

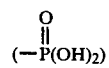

or a sulfonic

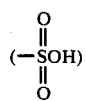

group and $R_2$ is hydrogen or a group represented by $R_1$.

| Chromatographic Parameters | |
|---|---|
| Column: | Partisil SAX, 25 cm × 4.5 mm i.d. |
| Column Temperature: | Ambient |
| Buffer: | Potassium Dihydrogen Phosphate (0.1 M; pH 2.8) |
| Buffer flow rate: | 1.5 ml/min |
| Pressure: | 1500 psi |

The chromatographic parameters are defined to allow the nitrosoamine to be measured to be eluted 2–3 minutes after the void volume of the column and the Greiss reactor. The ionic strength of the buffer will vary with the particular column employed. A column having less retention than a Partisil SAX column will require lower potassium acid phosphate buffer strength. If the nitrosoamine exists in isomeric forms, low levels of methanol may be used in the buffer. The use of 17% methanol in the buffer is recommended to coalesce the peaks of the two isomers and give one peak of good symmetry. The Waters 440 detector is operated at 0.01 AUFS in conjunction with a Spectrum 1021A filter amplifier with a cut-off frequency setting of 0.01 and a gain setting of 2 to give 0.005 AUFS. Under these conditions, baseline noise is less than 2% and an injection of 10 ng of a nitrosoamine gives a peak of 15–20% full scale. The sample containing the nitrosoamine to be determined is injected into the chromatographic system and the eluant containing the separated nitrosoamine is directly fed into a Technicon "Autoanalyzer ®".

Colormetric Procedure

The eluant stream from the high pressure liquid chromatograph is immediately segmented with 0.23 ml/min of air into 30 segments/min. To the segmented stream is added the N-(1-naphthyl)ethylenediamine dihydrochloride/hydrogen bromide and sulfanilamide/hydrochloride acid/Brij 35 reagents at a combined flow rate of 1.23 ml/min. The combined reagent stream results from mixing N-(1-naphthyl)ethylenediamine dihydrochloride/hydrogen bromide at 0.23 ml/min and sulfanilamide/hydrochloric acid/Brij 35 at 1.00 ml/min for 60 seconds prior to its addition to the segmented stream. The combined segmented stream is pumped through a mixing coil for 90 seconds to insure more complete mixing and then through a heated coil (90° C.) for approximately 6 minutes. The reaction stream is then passed through a cooling coil, debubbled and the absorbance of the complex is measured at a wavelength of 546 nm in a Waters Model 440 Detector equipped with a flow-through cell.

Sample quantitation is based on the relative peak height or peak area of the sample to standard peak heights or areas across the ranges of expected sample concentrations.

It is well understood by those skilled in the art that the range of nitrosoamine that may be measured in the above method is not limiting since larger amounts of nitrosoamine can be determined using proper dilution of the original sample.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method for quantitatively determining the nitrosoamine content of a sample containing a nitrosoamine which comprises sequentially the steps of:
   (a) separating said nitrosoamine from said sample by employing chromatographic means;
   (b) admixing said separated nitrosoamine with a composition comprising hydrogen bromide, sulfanilamide, hydrochloric acid, Brij 35 surfactant, said Brij 35 surfactant comprising polyoxyethylene (23) lauryl ether, and N-(1-naphthyl)ethylenediamine hydrochloride whereby a stable colored complex is formed which is readily detectable employing spectrophotometric means.

2. A method according to claim 1 wherein the chromatographic means consists of high pressure liquid chromatography.

3. The process of claim 1, wherein said nitrosoamine comprises a polar substituted alkyl nitrosoamine.

4. The process of claim 3, wherein said polar substituted alkyl nitrosoamine comprises a compound of the formula

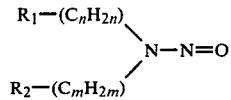

wherein n and m are independently integers from 1 to 6 and $R_1$ is a carboxy (—COOH), phosphonic

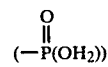

or a sulfonic

group and $R_2$ is hydrogen or a group represented by $R_1$.

* * * * *